DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 27, 1973

908 O.G. 790

T908,009

PROCESS OF PREPARING SUBSTITUTED p-(HYDROXYPHENYL) ACETIC ACIDS

James C. Martin, 601 N. Mountain View Circle, Johnson City, Tenn. 37601, and Paul G. Gott, 1017 Watauga St., Kingsport, Tenn. 37660

Filed Dec. 8, 1971, Ser. No. 206,178

Int. Cl. C07c *65/02*

U.S. Cl. 260—521 R

No Drawing. 12 Pages Specification

Certain substituted p-(hydroxyphenyl)acetic acids, typified by 2-methyl-2-(p-hydroxyphenyl) propionic acid, may be prepared by hydrogenation of the mono-beta-lactones prepared from disubstituted ketenes and p-quinones, at temperatures within the range of 0–150° C. and pressures ranging from one to several hundred atmospheres in the presence of a hydrogenation catalyst such as palladium, platinum, rhodium, ruthenium or nickel. The acid products obtained by the process may be readily converted by well-known autopolymerization procedures to polyesters useful in the production of clear, transparent sheets, films, filaments, fibers, molded articles and other valuable articles of commerce having excellent physical properties.